(12) United States Patent
Bogdanovic

(10) Patent No.: US 6,339,174 B1
(45) Date of Patent: Jan. 15, 2002

(54) METHOD FOR PREPARING ALDEHYDES BY HYDROFORMYLATION

(75) Inventor: Sandra Bogdanovic, Frankfurt am Main (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 09/508,542

(22) PCT Filed: Aug. 29, 1998

(86) PCT No.: PCT/EP98/05491

§ 371 Date: May 16, 2000

§ 102(e) Date: May 16, 2000

(87) PCT Pub. No.: WO99/13982

PCT Pub. Date: Mar. 25, 1999

(30) Foreign Application Priority Data

Sep. 16, 1997 (DE) .......................... 197 40 672

(51) Int. Cl.⁷ ..................... C07C 45/50; C07F 9/50
(52) U.S. Cl. ................. 568/454; 568/17; 568/451; 536/4.1; 536/18.5; 556/16; 556/21; 556/136
(58) Field of Search ................ 568/8, 16, 17, 568/451, 454; 536/4.1, 18.5, 55.3; 556/14, 16, 21, 136

(56) References Cited

U.S. PATENT DOCUMENTS

| 4,159,999 A | * 7/1979 | Stautzenberger et al. ... 260/604 HF |
| 4,329,511 A | 5/1982 | Hackman et al. |
| 5,091,350 A | * 2/1992 | Cornils et al. ............... 502/24 |

FOREIGN PATENT DOCUMENTS

| EP | 0068499 | 1/1983 |
| FR | 2291960 | 6/1976 |
| FR | 2314910 | 1/1977 |
| WO | 9522405 | 8/1995 |
| WO | 9830526 | 7/1998 |
| WO | 9830527 | 7/1998 |

* cited by examiner

*Primary Examiner*—S Padmanabhan
(74) *Attorney, Agent, or Firm*—Bierman, Muserlian and Lucas

(57) ABSTRACT

A catalyst composition comprising a) more than 70% by weight of a polyethylene glycol of the formula $H-(OCH_2-CH_2)_n-OH$, where n is an integer of 3 to 16 and the number average molecular weight is less than 650 b) rhodium in elemental form or bound form and c) 2 to 25% by weight of water soluble sulfonated triarylphosphine ligand having 1 to 2 phophorus atoms and not more than 25% by weight of water based on the total amount of the catalyst and its use for the hydroformylation of olefins to aldehydes is described.

20 Claims, No Drawings

METHOD FOR PREPARING ALDEHYDES BY HYDROFORMYLATION

This application is a 371 of PCT/EP98/05491 filed Aug. 28, 1998.

The present invention relates to a catalyst and to its use for the hydroformylation of olefinically unsaturated compounds having from 9 to 18 carbon atoms using hydrogen and carbon monoxide at superatmospheric pressure.

It is known that metals of group VIII of the Periodic Table of the Elements can be used for catalyzing addition reactions onto olefinically unsaturated compounds. The catalyst is frequently used as a solid which is insoluble in the reaction medium (heterogeneous catalysis).

One catalytic addition reaction of the olefins which is important from the point of view of industrial utility is hydroformylation. Here, aldehydes and alcohols are prepared by reaction of olefins with carbon monoxide and hydrogen, with the aldehydes and alcohols containing one more carbon atom than the starting olefin. The catalyst used is customarily used in a homogeneous phase with the olefin. The reaction is preferably catalyzed by hydridometal carbonyls of metals of group VIII of the Periodic Table. Apart from cobalt, which is widely used industrially as catalyst metal, rhodium has achieved increasing importance for, preferably, the hydroformylation of lower olefins. In contrast to cobalt, rhodium allows the reaction to be carried out at low pressure, and, in addition, straight-chain n-aldehydes are preferentially formed when using terminal olefins and iso-aldehydes are formed only in subordinate amounts. Furthermore, the hydrogenation of the olefinic compounds to form saturated hydrocarbons occurs to a significantly lesser extent in the presence of rhodium catalysts than when cobalt catalysts are employed.

In the processes introduced in the industry, the rhodium catalyst is used in the form of modified hydridorhodium carbonyls which contain additional ligands which may be used in excess. Ligands which have been found to be particularly useful are tertiary phosphines or phosphites. Their use makes it possible to reduce the reaction pressure to values below 30 MPa. However, the separation of the reaction products and the recovery of the catalysts dissolved homogeneously in the reaction product present problems in this process. In general, the reaction product is distilled from the reaction mixture. However, owing to the thermal sensitivity of the aldehydes and alcohols formed, this route can be employed in practice only in the hydroformylation of short-chain olefins. Here and in the following, the term "short-chain olefins" refers to olefins having not more than 8 carbon atoms in the molecule. The hydroformylation of long-chain olefins or olefinic compounds having functional groups forms products which have a high boiling point and cannot be separated by distillation from the homogeneously dissolved rhodium catalyst complex. The thermal stress on the material being distilled leads to thick oil formation and thus to considerable losses of desired products and of catalyst by decomposition of the rhodium complexes. Here and in the following, the term "long-chain olefins" refers to olefins having more than 8 carbon atoms in the molecule.

The problem of thermal decomposition is avoided if two-phase catalysis is used. Here, there are two liquid, mutually immiscible phases of which one, namely the organic phase, comprises the olefin and the other, usually polar phase, comprises the catalyst. Solubility of the catalyst in the polar phase is a prerequisite for use of this process. On an industrial scale, an aqueous phase is used as polar phase and a rhodium complex is used as catalyst. The solubility of the catalyst in the aqueous phase is achieved here by use of sulfonated triarylphosphines as constituents of the complex. In this process variant, the catalyst is separated from the reaction product after the hydroformylation reaction is complete simply by separation of aqueous and organic phases, i.e. without distillation and thus without additional thermal process steps. Such a process is described, for example, in DE-C 26 27 354. A particular feature of this procedure is that n-aldehydes are formed with high selectivity from terminal olefins and only subordinate amounts of iso-aldehydes (i.e. aldehydes branched in the α position relative to the aldehyde group) are formed. Besides sulfonated triarylphosphines, carboxylated triarylphosphines are also used as constituents of water-soluble rhodium complexes.

The use of water-soluble catalysts has also proven useful in the hydroformylation of lower olefins, in particular propene and butene. However, if higher olefins such as pentene or hexene are used, the reaction rate decreases noticeably. The economics of the reaction on an industrial scale are frequently no longer satisfactory when using olefins having more than four carbon atoms. In order to increase the conversion and/or the selectivity of the reaction to n-aldehydes in the hydroformylation of higher olefins by means of water-soluble catalysts, specific amphiphilic reagents or solubilizers have also been used. The addition of these materials leads to an improvement in mass transfer between the individual phases and thus the miscibility of aqueous catalyst phase and organic phase.

Thus, DE 31 35 127 A1 describes the hydroformylation of olefins using amphiphilic reagents. Table 7 shows that the hydroformylation of 1-dodecane by means of rhodium and monosulfonated triphenylphosphine ($3-Ph_2PC_6H_4SO_3Na$) without addition of an amphiphilic reagent leads to a conversion of 56% (Example 77), while the addition of a specific, long-chain alkyl ethoxylate of the formula $C_{12}H_{25}(OCH_2CH_2)_{23}OH$ (marketed by ICI Chemicals under the trade name Brij 35®) leads to a reduction in the conversion to 37% (Example 78).

DE 34 12 335 likewise relates to the hydroformylation of olefins using quaternary ammonium salts. As can be seen from Table 4, the hydroformylation of hexene by means of rhodium and trisodium tri(m-sulfophenyl)phosphine without addition of a solubilizer leads to a conversion of 36% (Example 10), while an addition of 2.5% of triethylene glycol (Example 14) or of 5% of polyglycol 200 (Example 11) gives a conversion of only 43.5% and 43%, respectively. In contrast, a very high conversion, namely 86%, is achieved by addition of 2.5% of trimethylhexadecylammonium bromide as solubilizer. This document shows that only the addition of quaternary ammonium salts results in an appreciable increase in the conversion. On the other hand, neither the addition of triglycols or polyglycols nor a doubling of the amount of these materials (from 2.5 to 5%) results in a significant increase in the conversion.

A disadvantage of the use of quaternary ammonium salts as amphiphilic reagents is, however, their poor biodegradability. Thus, for example, the presence of quaternary ammonium salts in wastewater leads to considerable difficulties in wastewater treatment. A further disadvantage of the use of amphiphilic reagents and solubilizers is that the increase in the miscibility of aqueous catalyst phase and organic phase achieved using these compounds is accompanied by an increased solubility of the organic phase in the aqueous phase and of the aqueous phase in the organic phase. In this way, amphiphilic reagent and solubilizer as well as rhodium and water-soluble phosphine can to an increasing extent get into the organic phase and be discharged with the organic phase after phase separation. The discharge of these substances via the organic phase is naturally undesirable, since corresponding amounts of new substances have to be added to the aqueous phase, which, particularly in respect of rhodium, is associated with considerably increased costs.

Furthermore, if relatively large amounts of amphiphilic reagents or solubilizers are added, i.e. the aqueous catalyst phase and the organic phase become increasingly miscible, the demixing required for phase separation no longer takes place or does not take place to an unsatisfactory extent as a result of the formation of emulsions or solutions. This occurs particularly in the case of those amphiphilic reagents which can also be used as surfactants or foam formers. This is a disadvantage since good demixing performance is an indispensable prerequisite for the necessary separation of organic and aqueous phases at the end of the hydroformylation.

It is an object of the invention to provide a catalyst for addition reactions onto olefinically unsaturated compounds, and also to provide for its use, in particular for preparing relatively long-chain aldehydes by hydroformylation of olefins. The use of this catalyst should make possible higher conversions compared to the prior art, avoid the disadvantages of the prior art and be able to be implemented on an industrial scale in a simple manner.

This object is achieved by a catalyst comprising
(a) more than 70% by weight of a polyethylene glycol of the formula (I)

where
n is an integer from 3 to 16; and
the number average molecular weight is less than 650;
(b) rhodium in elemental or bound form;
(c) from 2 to 25% by weight of a ligand containing at least 1 phosphorus atom;
(d) not more than 25% by weight of water.

The catalyst of the invention is particularly suitable for the catalysis of carbonylations or hydrogenations of olefinically unsaturated compounds, for example alkoxycarbonylations, hydroxycarbonylations or hydrosulfinations, in particular hydroformylation.

The catalyst of the invention is particularly notable for the fact that, despite the very high concentration of the polyethylene glycol of the formula (I), no significant increase in the amount of rhodium or ligand in the organic phase and thus no increased discharge of the catalyst via the organic phase is observed. In addition, organic phase and aqueous catalyst phase demix so readily that rapid separation of organic phase and aqueous phase is ensured. When using this catalyst, neither difficult-to-separate emulsions nor homogeneous solutions which cannot be separated are formed. These properties of the catalyst of the invention are surprising because polyethylene glycols of the formula (I) are customarily used as solubilizers in the prior art.

In a preferred embodiment of the invention, the catalyst comprises not more than 95% by weight of the polyethylene glycol of the formula (I). In particular, it can comprise from 80 to 85% by weight of the polyethylene glycol of the formula (I). Polyethylene glycols which are particularly suitable for the catalyst of the invention are those having a number average molecular weight of from 150 to 200.

Examples of compounds of the formula (I) are polyethylene glycols having a mean molecular weight of about 200 (PEG 200), 400 (PEG 400) or 600 (PEG 600).

For these polyethylene glycols, the terms have the following meanings:

PEG 200 is a mixture of polyethylene glycols of the formula $H(OCH_2CH_2)_nOH$ in which n is an integer from 3 to 6;

PEG 400 is a mixture of polyethylene glycols of the formula $H(OCH_2CH_2)_nOH$ in which n is an integer from 7 to 10;

PEG 600 is a mixture of polyethylene glycols of the formula $H(OCH_2CH_2)_nOH$ in which n is an integer from 11 to 16.

These mixtures have a corresponding mean molecular weight of about 200 (PEG 200), about 400 (PEG 400) or about 600 (PEG 600).

The ligand is preferably a water-soluble organic phosphine. Phosphines which have been found to be particularly useful for the process of the invention are trisulfonated triarylphosphines of the formula (II)

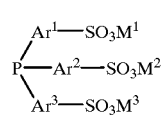

where
$Ar^1$, $Ar^2$ and $Ar^3$ are each, independently of one another, a phenyl, naphthyl, biphenyl, phenyinaphthyl or binaphthyl radical;
$M^1$, $M^2$ and $M^3$ are each, independently of one another, an alkaline metal ion or an ammonium ion.

However, it is also possible for $M^1$, $M^2$ and $M^3$ to be other cations bearing a higher charge, for example alkaline earth or zinc cations, in which case the need for electrical neutrality determines the number of these cations.

In a preferred embodiment of the present invention, this sulfonated triarylphosphine of the formula (II) is a trisulfonated triarylphosphine, in particular trisodium tri(m-sulfophenyl)phosphine of the formula

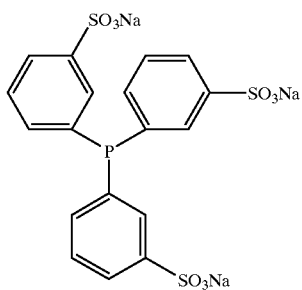

Owing to its preparation by sulfonation of triphenylphosphine, this trisodium salt additionally contains proportions of monosulfonated and disulfonated compounds and small amounts of the corresponding phosphine oxides.

When using ligands containing at least one phosphorus atom, in particular ligands of the formula (II), it has been found to be useful for the catalyst to contain from 10 to 1000 ppm, preferably from 200 to 500 ppm, in particular from 300 to 400 ppm, of rhodium. The ratio of rhodium to ligand can here be from 1:10 to 1:1000, preferably from 1:50 to 1:200.

The organic phosphine can also be a sulfonated triarylphosphine having two phosphorus atoms and comprising, for example, a $-(CH_2)_x-Ar-Ar-(CH_2)_x-$ radical, where x is an integer from 1 to 4, in particular 1 or 2, preferably 1;

Ar—Ar is biphenyl or binaphthyl;

the —$(CH_2)_x$— group is attached by one bond to the respective aryl radical in the ortho position relative to the aryl-aryl bond Ar—Ar connecting the two aryl radicals and is attached by the other bond to a phosphorus atom which in each case bears two further, identical or different aryl radicals, in particular phenyl radicals.

Examples of such sulfonated triarylphosphines containing two phosphorus atoms are compounds of the formula (III)

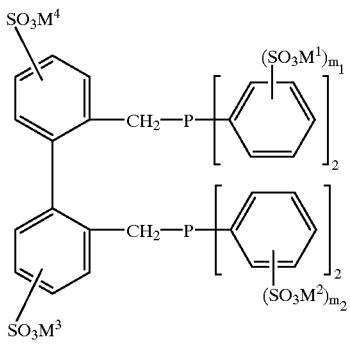

(III)

where $m^1$ and $m^2$ may be 0 or 1, and the sum of $m^1$ and $m^2$ is at least 1; and $M^1$, $M^2$, $M^3$ and $M^4$ are each, independently of one another, an alkaline metal ion or an ammonium ion.

However, it is also possible for $M^1$, $M^2$, $M^3$ and $M^4$ to be other cations bearing a higher charge, for example alkaline earth or zinc cations, in which case the need for electrical neutrality determines the number of these cations.

The organic phosphine containing two phosphorus atoms can equally well be a compound of the formula (IV)

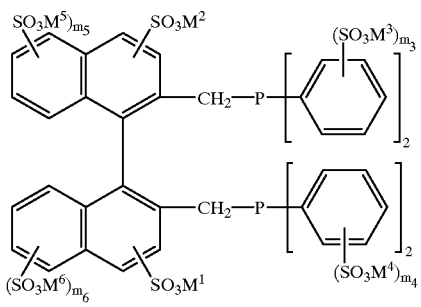

(IV)

where $m_3$, $m_4$, $m_5$ and $m_6$ may be 0 or 1, and the sum of $m_3$, $m_4$, $m_5$ and $m_6$ is at least 2; and $M^1$, $M^2$, $M^3$, $M^4$, $M^5$ and $M^6$ are each, independently of one another, an alkaline metal ion or an ammonium ion. Here too, it is possible for $M^1$, $M^2$, $M^3$, $M^4$, $M^5$ and $M^6$ to be other cations bearing a higher charge, for example alkaline earth or zinc cations, where the need for electrical neutrality determines the number of these cations.

When using ligands of the formulae (III) and (IV), it has been found to be useful for the catalyst to contain from 20 to 500 ppm, preferably from 30 to 150 ppm, in particular from 40 to 100 ppm, of rhodium. The ratio of rhodium to ligand can here be from 1:5 to 1:100, preferably from 1:5 to 1:50, in particular from 1:8 to 1:15. Such triarylphosphines of the formulae (III) and (IV) containing two phosphorus atoms have, in particular, from four to eight —$SO_3M$ groups. The —$SO_3M$ groups are usually located on the aryl radicals of the —$(CH_2)_x$—Ar—Ar—$(CH_2)_x$— radical and on the two further aryl radicals which are connected to the phosphorus.

Alternatively, in place of sulfonated triarylphosphines, the ligands used can be other triarylphosphines in which the $SO_3M$ group is replaced by other groups which make the triarylphosphine water-soluble, e.g. $PO_3M_2$ groups.

In a particularly preferred embodiment, the catalyst can be used for preparing relatively long-chain aldehydes by hydroformylation of an olefin having from 9 to 18 carbon atoms, in particular 12 to 14 carbon atoms. The olefin can be selected from among aliphatic, cycloaliphatic and araliphatic olefins, in particular from among aliphatic and cycloaliphatic α-olefins. The olefinic compound can contain one or more carbon-carbon double bonds. The carbon-carbon double bond may be terminal or internal. Preference is given to olefinic compounds having a terminal carbon-carbon double bond. Examples of α-olefinic compounds (having a terminal carbon-carbon double bond) are 1-alkenes, alkyl alkenoates, alkylene alkanoates, alkenyl alkyl ethers and alkenols. Without making any claim as to completeness, examples of α-olefinic compounds are 1-dodecene, 1-tetradecene, 1-hexadecene and 1-octadecene. Further examples of suitable olefinic compounds are diisobutylene, tripropylene, Octol or Dimersol (dimerization products of butenes), tetrapropylene, acyclic, cyclic or bicyclic terpenes such as myrcene, limonene and pinene. With regard to industrial use of the process, the olefin is particularly preferably selected from the group consisting of 1-nonene, 1-decene, 1-undecene, 1-dodecene, 1-tetradecene, 1-hexadecene and 1-octadecene.

In a particularly preferred embodiment of the process of the invention, the olefin is present in a liquid, water-immiscible phase under the reaction conditions. The catalyst-containing aqueous phase can be prepared in a comparatively simple way by dissolving a water-soluble rhodium salt, the sulfonated triarylphosphines and the compound of the formula (I) in water. Suitable rhodium salts are, without making any claim as to completeness: rhodium(III) sulfate, rhodium(III) nitrate, rhodium(III) carboxylates such as rhodium(III) acetate, rhodium propionate, rhodium butyrate and rhodium 2-ethylhexanoate. The aqueous phase can be used directly in the hydroformylation or can be subjected beforehand to preformation of the catalyst under reaction conditions in order to use it subsequently in the preformed state. The catalyst-containing phase is preferably used in an amount of from $2 \times 10^{-6}$ to $5 \times 10^{-2}$ mol of rhodium per mol of olefinic compound.

The pressure during the reaction is generally from 20 to 150 bar, preferably from 30 to 80 bar; carbon monoxide and hydrogen can be added under a pressure of from 5 to 30 MPa, preferably from 10 to 18 MPa. The ratio of carbon monoxide to hydrogen can be varied within wide limits. It is useful to employ a ratio of carbon monoxide to hydrogen of from 10:1 to 1:30, in particular from 5:1 to 1:8, particularly preferably from 1:2 to 1:5. It is likewise advantageous to inject synthesis gas in a ratio of carbon monoxide to hydrogen of from 1:1 to 1:5, in particular from 1:1 to 1:3, and, if necessary, later to inject pure hydrogen during the course of the reaction. The temperature is usually in the range from 50 to 150° C., preferably from 100 to 140° C.

As reaction vessels, use is made of pressure reactors having a magnetic or mechanical stirring or mixing device. Good mixing of the phases present, i.e. of the polar phase, carbon monoxide/hydrogen and, if present, the organic phase, has to be ensured during the reaction. This can be achieved, in particular, by intensive stirring and/or pumped circulation of organic and aqueous phases. It is likewise possible to carry out the process continuously.

After the reaction is complete, the pressure reactor is cooled, freed of carbon monoxide and hydrogen by releasing the pressure, and the reaction mixture is taken out. When the mixing device is switched off, the phases separate spontaneously within seconds. The organic, phase can be worked up by distillation and then, if required, analyzed by gas chromatography.

The following examples serve to illustrate the invention.

EXAMPLE 1

(Comparative example)

a): Preparation of the catalyst phase and preformation 30 mg (0.166 mmol) of rhodium(III) acetate are dissolved in 19.5 ml of a 0.6 M aqueous solution of the trisodium salt of TPPTS (tris(meta-sulfonato) triphenylphosphine), corresponding to a molar ratio of rhodium to ligand of 1:100, and 10.5 ml of degassed, distilled water, and introduced under a stream of nitrogen into a 200 ml steel autoclave. The catalyst solution prepared in this way is heated at 125° C. under a synthesis gas pressure of 25 bar ($CO/H_2=1/1$) for 3 hours, forming the active catalyst complex. The solution becomes an intense yellow color.

b): Hydroformylation 120 mmol of 1-nonene are added to the preformed catalyst solution from 1.a) under a reaction pressure of 30 bar and at 125° C. via an upstream 200 ml steel autoclave under a slight overpressure. The ratio of olefin to rhodium is 1030:1. The hydroformylation reaction is started by switching on the magnetic stirrer. During a reaction time of 3 hours, the temperature is held at 125° C. and the reaction pressure is kept constant within a pressure band of ±3 bar by manual introduction of synthesis gas. After 3 hours, stirrer and heating are switched off, the autoclave is cooled to 40–50° C. and the upper product phase is separated from the catalyst phase by phase separation in a separating funnel. Product phase and catalyst phase are weighed. The composition of the product phase is determined by means of gas chromatography and $^1$H-NMR spectroscopy, and the yield of hydroformylation products and the ratio of n-decanal to iso-decanal are determined from the composition. The yield of hydroformylation products is 4.3% and the n/iso ratio is 96:4.

EXAMPLE 2

The procedure of Example 1 is repeated, except that the catalyst phase is made up from 30 mg of rhodium(III) acetate, 19.5 ml of a 0.6 M aqueous solution of the trisodium salt of TPPTS (tris(meta-sulfonato)triphenyl-phosphine), corresponding to a molar ratio of rhodium to ligand of 1:100, and 50 ml of PEG 150, and a total of 15.7 ml of water are distilled from this mixture under reduced pressure. The catalyst phase thus contains 89.5% by weight of PEG 150.

EXAMPLES 3 to 16

Comparative Examples 3, 6 and 14 are carried out using a method analogous to Example 1. Examples 4, 5, 7 to 13, 15 and 16 according to the invention are carried out using a method analogous to Example 2. In all examples, 30 mg (0.166 mmol) of rhodium(III) acetate, 19.5 ml of a 0.6 M aqueous solution of the trisodium salt of TPPTS (tris(meta-sulfonato)triphenylphosphine), corresponding to a molar ratio of rhodium to ligand of 1:100, and 120 mmol of the appropriates olefin are used. The ratio of olefin to rhodium is 1030:1 in all examples. The further starting materials and their amounts and also the results of the reaction are shown in Table 1.

In Table 1, the following terms/abbreviations are used:

"Olefin" refers to the olefin used; Rh represents rhodium (III) acetate;

"$H_2O$ dist." is the amount of water distilled off from the catalyst phase, in ml;

"PEG" refers to the polyethylene glycol used; here, the number given in the table is the number average molecular weight of the respective polyethylene glycol. The amount of polyethylene glycol used in each of the Examples 4, 5, 7 to 13, 15 and 16 is 50 ml.

"Amount" is the amount of polyethylene glycol in the catalyst phase, in % by weight;

"t" is the reaction time in minutes;

"n:iso" is the ratio of n-aldehydes to iso-aldehydes; "n.d." (not able to be determined) here means that the ratio cannot be determined because of the low conversion.

TABLE 1

| Example | Olefin | PEG | $H_2O$ dist. [ml] | Amount [% by weight] | t [min] | Conversion [%] | n:iso |
|---|---|---|---|---|---|---|---|
| 1* | 1-nonene | — | — | — | 180 | 4.3 | 96:4 |
| 2 | 1-nonene | PEG 150 | 15.7 | 89.5 | 50 | 95.3 | 98:2 |
| 3* | 1-decene | — | — | — | 240 | 1.5 | nd |
| 4 | 1-decene | PEG 150 | 12.7 | 85.5 | 60 | 91.5 | 97:3 |
| 5 | 1-decene | PEG 150 | 15.7 | 89.5 | 35 | 92.04 | 98:2 |
| 6* | 1-dodecene | — | — | — | 180 | <1 | n.d. |
| 7 | 1-dodecene | PEG 400 | 10 | 82.2 | 180 | 52.2 | 72:28 |
| 8 | 1-dodecene | PEG 200 | 12 | 84.7 | 180 | 75.0 | 72:28 |
| 9 | 1-dodecene | PEG 200 | 12.7 | 85.5 | 120 | 81.5 | 73:27 |
| 10 | 1-dodecene | PEG 200 | 15.7 | 89.5 | 120 | 83.0 | 79:21 |
| 11 | 1-dodecene | PEG 150 | 10 | 82.2 | 180 | 76.3 | 76:27 |
| 12 | 1-dodecene | PEG 150 | 12 | 84.7 | 180 | 81.6 | 73.27 |
| 13 | 1-dodecene | PEG 150 | 15.7 | 89.5 | 70 | 73.3 | 72 28 |
| 14* | 1-octadecene | — | — | — | 180 | 0 | n.d. |
| 15 | 1-octadecene | PEG 150 | 12.7 | 85.5 | 440 | 47.3 | 73.27 |
| 16 | 1-octadecene | PEG 150 | 15.7 | 89.5 | 440 | 61.7 | 71:29 |

*Comparative example

What is claimed is:

1. A composition of a catalyst comprising a) more than 70% by weight of a polyethylene glycol of the formula

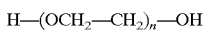

H—(OCH$_2$—CH$_2$)$_n$—OH     I wherein n is an integer of 3 to 16 and the number average molecular weight is less than 650 b) rhodium in elemental or bound form and c) 2 to 25% by weight of water-soluble sulfonated triarylphosphine ligand having 1 to 2 phosphorous atoms and not more than 25% by weight of water based on the total amount of the catalyst.

2. A composition of claim 1 wherein the catalyst contains not more than 95% by weight of the polyethylene glycol.

3. A composition of claim 1 wherein the catalyst contains 80 to 85% by weight of polyethylene glycols.

4. A composition of claim 1 wherein the sulfonated triarylphosphine has the formula

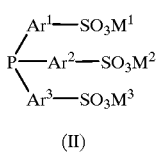

(II)

wherein Ar$^1$, Ar$^2$ and Ar$^3$ are individually selected from the group consisting of phenyl, naphthyl, biphenyl, phenylnaphthyl and binaphthyl and M$^1$, M$^2$ and M$^3$ are individually an alkali metal ion or ammonium ion.

5. A composition of claim 4 wherein the sulfonated triarylphosphine is trisodium tri(m-sulfophenyl) phosphine.

6. A composition of claim 1 wherein the catalyst contains 100 to 1000 ppm of rhodium.

7. A composition of claim 1 wherein the molar ratio of rhodium to ligand is 1:10 to 1:1000.

8. A composition of claim 1 wherein the water-soluble sulfonated triarylphosphine has the formula

III

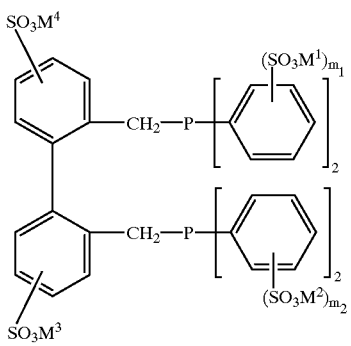

wherein m$^1$ and M$^2$ are 0 or 1 and m$^1$+m$^2$ is at least 1 and M$^1$, M$^2$, M$^3$ and M$^4$ are individually an alkali metal ion or an ammonium ion.

9. A composition of claim 1 wherein the water-soluble sulfonated triarylphosphine has the formula

IV

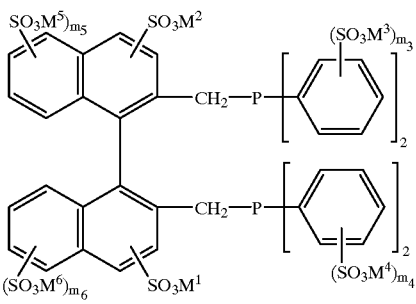

wherein m$^3$, m$^4$, m$^5$ and m$^6$ are 0 or 1 and m$^3$+m$^4$+m$^5$+m$^6$ is at least 2 and M$^1$, M$^2$, M$^3$, M$^4$, M$^5$ and M$^6$ are individually an alkali metal ion or an ammonium ion.

10. A composition of claim 8 containing 20 to 500 ppm of rhodium.

11. A composition of claim 9 containing 20 to 500 ppm of rhodium.

12. A composition of claim 8 wherein the molar ratio of rhodium to ligand is 1:5 to 1:100.

13. A composition of claim 9 wherein the molar ratio of rhodium to ligand is 1:5 to 1:100.

14. In a process for the preparation of aldehydes by heterogenous hydroformylation of an olefin of 9 to 18 carbon atoms with hydrogen and carbon monoxide in the presence of a catalyst, the improvement comprising using as the catalyst, the composition of claim 1.

15. The process of claim 14 wherein the olefin is selected from the group consisting of aliphatic olefins, cycloaliphatic olefins and araliphatic olefins.

16. The process of claim 14 wherein the olefin is selected from the group consisting of 1-nonene, 1-decene, 1-undecene, 1-dodecene, 1-tetradecene, 1-hexadecene and 1-octadecene.

17. The process of claim 14 wherein the olefin is present during reaction in a liquid phase immiscible with the catalyst composition.

18. The process of claim 14 wherein the molar ratio of rhodium to olefin is $2 \times 10^{-6}$ to $5 \times 10^{-2}$.

19. The process of claim 14 wherein the hydroformylation is effected at a pressure of 20 to 150 bar.

20. The process of claim 14 wherein the hydroformylation is effected at 50 to 150° C.

* * * * *